(12) United States Patent
Fanizza et al.

(10) Patent No.: US 9,173,830 B1
(45) Date of Patent: Nov. 3, 2015

(54) SUNSCREEN COMPOSITIONS

(71) Applicant: Avon Products, Inc., Suffern, NY (US)

(72) Inventors: Juliana Fanizza, Warwick, NY (US);
Ashley L. Howell, Oakland, NJ (US);
William E. McNamara, Chester, NY (US)

(73) Assignee: Avon Products, Inc, New York, NY (US)

( * ) Notice: Subject to any disclaimer, the term of this patent is extended or adjusted under 35 U.S.C. 154(b) by 48 days.

(21) Appl. No.: 14/260,775

(22) Filed: Apr. 24, 2014

(51) Int. Cl.
*A61Q 17/04* (2006.01)
*A61K 8/02* (2006.01)
*A61K 33/04* (2006.01)
*A61K 47/00* (2006.01)
*A61K 8/88* (2006.01)
*A61K 8/25* (2006.01)
*A61K 8/23* (2006.01)
*A61K 8/37* (2006.01)
*A61K 8/35* (2006.01)
*A61K 8/40* (2006.01)

(52) U.S. Cl.
CPC ... *A61K 8/88* (2013.01); *A61K 8/23* (2013.01); *A61K 8/25* (2013.01); *A61K 8/35* (2013.01); *A61K 8/37* (2013.01); *A61K 8/40* (2013.01); *A61Q 17/04* (2013.01); *A61K 2800/262* (2013.01); *A61K 2800/43* (2013.01); *A61K 2800/54* (2013.01); *A61K 2800/591* (2013.01); *A61K 2800/614* (2013.01); *A61K 2800/652* (2013.01)

(58) Field of Classification Search
None
See application file for complete search history.

(56) References Cited

U.S. PATENT DOCUMENTS

| 6,210,658 | B1 | 4/2001 | Bonda |
| 2007/0253989 | A1 | 11/2007 | Abe et al. |
| 2009/0258230 | A1 | 10/2009 | Schlossman et al. |
| 2010/0202985 | A1 | 8/2010 | Sengupta |
| 2010/0266647 | A1 | 10/2010 | Dingley et al. |
| 2012/0045579 | A1 * | 2/2012 | Sojka et al. .................. 427/222 |

FOREIGN PATENT DOCUMENTS

WO   WO 2009/050605 A2 *   4/2009   ............ C01B 33/148

* cited by examiner

*Primary Examiner* — Jeffrey T Palenik
(74) *Attorney, Agent, or Firm* — David M. Joyal; Jean M. McGillycuddy

(57) ABSTRACT

Compositions comprising an organic sunscreen in combination with (i) nylon particles, (ii) silica particles, and (iii) barium sulfate particles provide an improvement in SPF as compared to an otherwise identical composition lacking any one of the three ingredients (i)-(iii). The compositions advantageously provide high diffuse transmittance, giving a natural look to the skin.

15 Claims, No Drawings

SUNSCREEN COMPOSITIONS

FIELD OF INVENTION

The invention relates generally to compositions and methods for protecting human integuments against damage from ultraviolet (UV) rays. More specifically, the invention relates to the use of a composition that boosts the sun protection factor (SPF) of an organic sunscreen.

BACKGROUND OF THE INVENTION

It is now generally recognized that exposure to solar radiation can have adverse health consequences, sometimes not appearing until several years following exposure. Of course, the immediately appearing sunburn from an overexposure is painful and can itself be a serious acute health problem.

Products are available to reduce the amount of solar UV radiation received by the skin during exposure to the sun's rays. Typical product formulations are lotions, sprays, creams, ointments, or gels containing chemical and/or physical barriers to ultraviolet transmission. These vary considerably in their abilities to protect the skin against the physical and biochemical effects of UV radiation.

Earlier sunscreen formulations were designed to protect against sunburn from a limited solar exposure period, while transmitting sufficient radiation to permit skin tanning. However, the current focus is on eliminating as much UV exposure as possible, it being recognized that skin tanning is an indication of tissue damage from overexposure to solar radiation. It is believed that any amount of unprotected exposure can lead to future health problems, such as skin carcinomas and other dermatological disorders. Sunscreens and UV filters are important components of skin care products generally to prevent the harmful rays of the sun from exacerbating or accelerating the aging process. These actives are typically present in an amount to provide a Sun Protection Factor (SPF) value of from 2 to about 50 or higher.

Many organic sunscreens are known in the art. Some examples include PABA, ethylhexyl-methoxycinnamate, homomethyl salicylate, octyl salicylate, and butyl methoxydibenzoylmethane (Avobenzone), and the like. Not only are these ingredients costly, but many sunscreen products have undesirable aesthetic attributes which may limit their use.

It is therefore an object of the invention to provide compositions for boosting the SPF of an organic sunscreen. It is a further object of the invention to provide compositions that impart protection against UV rays while providing desirable aesthetics on the skin.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that compositions comprising an organic sunscreen in combination with (i) nylon particles (e.g., porous nylon-6 particles treated with hydrogen dimethicone or non-porous nylon-12 particles), (ii) silica particles (e.g., spherical silica particles), and (iii) barium sulfate particles can provide an improvement in SPF as compared to an otherwise identical composition lacking any one of the three ingredients (i)-(iii). In some embodiments, the improvement is synergistic by which is meant that the improvement in SPF is more than additive of the improvement in SPF seen when components (i)-(iii) are employed individually. In some embodiments, the SPF of the composition is at least about 10% greater, at least about 20% greater, at least about 30% greater, at least about 40% greater, or at least 50% greater or more than the SPF of an otherwise identical composition lacking any one of components (i)-(iii).

The compositions of the invention typically comprises an organic sunscreen. In one embodiment, the composition may comprise ethylhexyl-methoxycinnamate (OMC), homosalate, octyl salicylate, Avobenzone, or any combination thereof. The amount of organic sunscreen may be, collectively or individually, from about 0.5% to about 50%, more typically from about 1% to about 20%, and more typically still from about 2.5% to about 15% by weight of the total composition. The composition may comprise nylon particles (e.g., porous nylon-6) in an amount from about 0.5% to about 20%, typically from about 1% to about 10%, or from about 2% to about 10%, or about 5% by weight of the total composition. The composition may comprise silica particles (e.g., spherical silica) in an amount from about 0.5% to about 20%, typically from about 1% to about 10%, or from about 1% to about 5%, or about 2.5% by weight of the total composition. The composition may comprise barium sulfate particles in an amount from about 0.5% to about 20%, typically from about 1% to about 10%, or from about 2% to about 10%, or about 5% by weight of the total composition. The weight ratio of nylon to silica to barium sulfate may be, for example, from about 5 to about 15 parts of nylon to from about 1 to about 10 parts of silica to from about 5 to about 15 parts of barium sulfate. In one embodiment, the weight ratio of nylon to silica to barium sulfate may be about 2:1:2. The composition may optionally comprise one or more colorants (e.g., pigments, lakes, dyes, etc.) In one embodiment the composition comprises iron oxide pigments (e.g., in an amount from about 0.1 to about 10% by weight). In another embodiment the composition comprises silica-coated iron oxide pigment particles (e.g., in an amount from about 0.1 to about 10% by weight). Also provided are methods for protecting a human integument against UV damage comprising applying a composition of the present invention to the human integument, including a keratinous surface such as skin or hair.

The compositions according to the invention advantageously provide high diffuse transmittance which contributes to a more natural appearance on the skin and also serves to blur fine lines and blemishes, contributing to an overall improvement in the appearance of human skin.

These and other aspects of the present invention will become apparent to those skilled in the art after a reading of the following detailed description of the invention, including the appended claims.

DETAILED DESCRIPTION OF THE INVENTION

All amounts provided in terms of weight percentage are relative to the entire composition (i.e., including solvent or vehicle) unless otherwise stated. It will be understood that the total of all weight percentages in a given composition will not exceed 100%.

The term "keratinous surface" includes skin, hair, lashes, and nails. The term "skin" is intended to include skin of the face, neck, chest, arms, hands, lips, etc.

The term "consisting essentially of" is intended to include only those components that do not materially alter the basic and novel features of the inventive compositions, including without limitation, the SPF and/or diffuse transmittance/soft focus of the cosmetic.

The compositions of the invention comprise a combination of particulates comprising polymeric particles (e.g., a polyamide such as porous nylon particles), silica particles (e.g., spherical silica particles), and barium sulfate particles (e.g., synthetic barium sulfate particles). The compositions further comprise an organic sunscreen (e.g., octyl methoxycinnamate, etc.).

One component of the present invention is a polymeric powder or particulate. In one embodiment, the polymeric powder or particulate comprises a polyamide (e.g., nylon) particulate material. In general, any polyamide particle is contemplated to be suitable, including nylon particles, such as nylon-6,6; nylon-6; nylon-6,9; nylon-6,10; nylon-6,12; nylon-10,10 (e.g., Tegolon® ECO from Evonik); nylon-11; nylon-12, and nylon-4,6, and the like. Nylon particles may be porous or non-porous, and/or spherical particles. In one embodiment, porous particles of nylon-6 (polycaprolactam) polymer may be used. The porous nylon particles may, for example, have a bulk density of less than 0.5 g/cc, or less than 0.45 g/cc, or less than 0.4 g/cc, or less than 0.35 g/cc, or less than about 0.3 g/cc. In another embodiment, non-porous particles of nylon-12 polymer may be used. The nylon particles may be surface treated to impart hydrophobicity. The surface treatment may comprise a hydrocarbon, fluorocarbon, and/or silicone chain. The chain may be covalently bound to the surface of the particle through any functional group, including, without limitation, a silane linkage. In one embodiment, nylon particles (e.g., porous nylon-6) may be treated with hydrogen dimethicone to provide water repellency. The size of the nylon particles may range from about 0.5 to about 40 microns in diameter, typically from about 2 to about 15 microns, or from about 3 to about 8 microns. Suitable porous nylon particles include POMP 605 and POMP 605-S101 from UBE Industries. One suitable non-porous nylon particle is SP-500 from Kobo Products, Inc.

Another component of the present invention is a silica particulate. Silica particles may range in average size from about 1 to about 100 microns, or from about 1 to about 40 microns, or from about 5 to about 15 microns. In one embodiment the silica particles have a size of about 12 microns. In one embodiment the silica particles are spherical silica particles. One suitable spherical silica particulate material is MSS-500W from Kobo Products. The silica particles may be optionally surface treated to increase oil and/or water repellency or to improve dispersion in the vehicle. In some embodiments, alumina particles, such as spherical alumina particles may be used in place of some or all of the silica particles. In other embodiments the compositions are free of alumina particles or are substantially free of alumina particles by which is meant that the composition contains less than 1% by weight, or less than 0.5% by weight, or less than 0.25% by weight, or less than 0.1% by weight of alumina particles.

Another component of the present invention is barium sulfate in particulate form. In one embodiment barium sulfate particles may be synthetically produced. Barium sulfate particles may be insoluble in water or organic solvents, resistant to acids and alkali, and color neutral due to their refractive index. In one embodiment, the average particle size of barium sulfate particles is greater than 0.1 micron, typically greater than 0.2 micron, more typically greater than 0.5 micron. In another embodiment, the median particle size of barium sulfate particles is from about 0.5 to about 40 microns, or from about 0.75 to about 25 microns, or from about 1 to about 10 microns, or about 3 microns. Examples of suitable barium sulfate particles are "USP Barium Sulfate for Formulation" from Mallinckrodt Inc or "Blanc Fixe XR-HN" from Sachtleben Chemie GmbH.

The compositions of the invention typically comprise one or more organic sunscreens. These may include, but are not limited to, water soluble sunscreens (such as Eusolex 232); oil soluble sunscreens (such as octyl methoxycinnamate); and other organic sunscreens (such as camphor derivatives, cinnamates, salicylates (e.g., octyl salicylate (octisalate), homomenthyl salicylate (homosalate)), benzophenones, paraaminobenzoic acid (PABA), PABA derivatives, including octyl dimethyl PABA and ethyl PABA, diphenylacrylate derivatives, and dibenzoylmethane derivatives such as butylmethoxy dibenzoylmethane (avobenzone), benzophenone-3 (oxybenzone), dioxybenzone, menthyl anthranilate, octocrylene, drometrizole trisiloxane, 4-methyl benzilidene camphor, octyl triazone, triazines, including hydroxy methylphenyl benzotriazole, methylene bisbenzotriazoyltetramethylbutylphenol, bis-ethylhexyloxyphenol methoxyphenol triazine, and mixtures thereof. The sunscreen may be present in the amount from about 1% to about 30% by weight of the total composition, typically from about 1% to about 10% by weight.

The compositions of the invention may optionally comprise one or more colorants. Suitable colorants include dyes, pigments, lakes and particulate fillers. In one embodiment, the composition includes from about 0.1% to about 10% by weight of a pigment, such as an inorganic oxide, including metal oxides such as iron oxide, titanium dioxide, zinc oxide, and the like.

Exemplary inorganic pigments include, but are not limited to, inorganic oxides and hydroxides such as magnesium oxide, magnesium hydroxide, calcium oxide, calcium hydroxides, aluminum oxide, aluminum hydroxide, iron oxides ($\alpha$-$Fe_2O_3$, $\gamma$-$Fe_2O_3$, $Fe_3O_4$, FeO) and iron hydroxides including red iron oxide, yellow iron oxide and black iron oxide, titanium dioxide, titanium lower oxides, zirconium oxides, chromium oxides, chromium hydroxides, manganese oxides, manganese hydroxides, cobalt oxides, cobalt hydroxides, cerium oxides, cerium hydroxides, nickel oxides, nickel hydroxides, zinc oxides and zinc hydroxides and composite oxides and composite hydroxides such as iron titanate, cobalt titanate and cobalt aluminate and the like. The inorganic pigment particles may contain optional coatings, such as, for example, silica, titania, and the like. In one embodiment, the pigments have a particle size from 5 nm to 500 microns, or from 5 nm to 250 microns, or from 10 nm to 100 microns. In some embodiments, the particle size (median) will be less than about 5 microns or less than 1 micron.

Additional exemplary color additives are lakes including, for example: D&C Red No. 19 (e.g., CI 45170, CI 73360 or CI 45430); D&C Red No. 9 (CI 15585); D&C Red No. 21 (CI 45380); D&C Orange No. 4 (CI 15510); D&C Orange No. 5 (CI 45370); D&C Red No. 27 (CI 45410); D&C Red No. 13 (CI 15630); D&C Red No. 7 (CI 15850:1); D&C Red No. 6 (CI 15850:2); D&C Yellow No. 5 (CI 19140); D&C Red No. 36 (CI 12085); D&C Orange No. 10 (CI 45475); D&C Yellow No. 19 (CI 15985); FD&C Red #40 (CI#16035); FD&C Blue #1 (CI#42090); FD&C Yellow #5 (CI#19140); or any combinations thereof.

Suitable fillers include without limitation silica, surface treated silica, talc, zinc stearate, mica, kaolin, nylon particles or powders such as Orgasol®, polyethylene particles or powder, PMMA powder, Teflon®, polymeric beads or powders, including copolymer microspheres such as Expancel® (Nobel Industries), Polytrap® (Dow Corning) and silicone resin microbeads (Tospearl® from Momentive) or silicone elastomeric particles, and the like. Additional pigment/powder fillers include, but are not limited to, inorganic powders such as gums, chalk, Fuller's earth, kaolin, sericite, muscovite, phlogopite, synthetic mica, lepidolite, biotite, lithia mica, vermiculite, aluminum silicate, starch, smectite clays, alkyl and/or trialkyl aryl ammonium smectites, chemically modified magnesium aluminum silicate, organically modified montmorillonite clay, hydrated aluminum silicate, fumed aluminum starch octenyl succinate barium silicate, calcium silicate, magnesium silicate, strontium silicate, metal tungstate, magnesium, silica alumina, zeolite, barium sulfate, calcined calcium sulfate (calcined gypsum), calcium phosphate, fluorine apatite, hydroxyapatite, ceramic powder, metallic soap (zinc stearate, magnesium stearate, zinc myristate, calcium palmitate, and aluminum stearate), colloidal silicone dioxide, and boron nitride; cyclodextrin, copolymer powder of styrene and acrylic acid, benzoguanamine resin powder, and carboxyvinyl polymer, starch, cellulose powder and modified cellulose powders such as hydroxyethyl cellulose and sodium carboxymethyl cellulose, cellulose beads, ethylene glycol monostearate; and stabilizers/rheology modifiers, for example, Bentone Gel and Rheopearl TT2.

The amount and type of the additional colorants and light diffusers used will vary depending upon the nature of the final product and the desired intensity of color; generally, however, the amount of such additional colorants typically will be about 0.01 wt % to about 75 wt %, and more typically from about 0.25 wt % to about 10 wt % or even 50 wt %, by weight of the total composition, depending on the nature of the final cosmetic.

The inventive combination of components described herein ideally provides improved optical blurring, soft focus, and high chroma. An optical diffuser is a particle that changes the surface optometrics of skin, resulting in a visual blurring and softening of, for example, lines and wrinkles Examples of optical diffusers that can be used in the present invention include, but are not limited to, boron nitride, mica, nylon, polymethylmethacrylate (PMMA), polyurethane powder, sericite, silica, silicone powder, talc, Teflon, titanium dioxide, zinc oxide, titania fibers, polyamide-6 powders or any mixtures thereof. When present, the optical diffuser may be present from about 0.01 wt % to about 20 wt % of the total weight of the composition.

In some embodiments, the compositions comprise an interference or pearlescent pigment, such as bismuth oxychloride or titanated mica. Pearls and interference pigments, when present, will typically comprise from about 0.1% to about 20% by weight of the total composition. In other embodiments the compositions of the present invention may be free of, or substantially free of interference pigments. Substantially free of interference pigments means less than about 1%, and preferably less than about 0.5%, and more preferred still less than about 0.1% by weight of the entire composition.

In some embodiments, the pigments, lakes, and/or fillers may be surface treated. The surface treatment may for example, make the particles more hydrophobic or more dispersible in a vehicle. The surface of the particles may, for example, be covalently or ionically bound to an organic molecule or silicon-based molecule or may be adsorbed thereto, or the particle may be physically coated with a layer of material. The surface treatment may comprise, in some embodiment, a material selected from aluminum laurate, aluminum stearate, an amino acid, chitin, collagen, fluorochemical, lecithin metal soap, natural wax, polyacrylate, polyethylene, silicone, silane, titanatate ester, urethane, dimethicone, perfluoropolymethylisopropyl ether, styrene acrylates copolymer, magnesium myristate, lauroyl lysine and a combination thereof. In other embodiments, the surface treatment comprises a material selected from methicone, triethoxycaprylyisilane, trimethoxycaprylylsilane, dimethicone copolyol and a combination thereof. In one embodiment, the particulate colorant has been surface treated with an alkylsilane, such as a $C_{1-20}$ alkylsilane, or more typically a $C_{1-12}$ alkylsilane, including an exemplary embodiment wherein the particle is surface-treated with a $C_8$ alkylsilane (e.g., caprylylsilane). The colorants may be prepared, for example, by treating a particulate with a trialkoxyalkylsdane, such as Triethoxycaprylyisilane (INCI) or Trimethoxycaprylyisilane (INCI). In another embodiment, the particulate has been surface treated with a fluoroalkylsilane, and in particular a perfluoroalkylsilane, such as a $C_{1-20}$ perfluoroalkylsilane, or more typically a $C_{1-12}$ perfluoroalkylsilane, including an exemplary embodiment wherein the particulate colorant is surface-treated with a $C_8$ perfluoroalkylsilane. These may be prepared by treating a particulate colorant with a trialkoxyfluoroalkylsilane, such as Perfluorooctyl Triethoxysilane (INCI). An example of such a compound is tridecafluorooctyltriethoxy silane.

The cosmetic compositions of the invention may optionally include one or more agents that provide or enhance shine. Shine enhancing agents will typically have a refractive index greater than about 1.4, preferably greater than about 1.5 when measured as a film at 25° C. Suitable shine enhancing agents include without limitation, polyols (e.g., glycerin), fatty esters, silicone oils, phenylpropyldimethylsiloxysilicate, polybutene, polyisobutene, hydrogenated polyisobutene, hydrogenated polycyclopentadiene, propyl phenyl silsesquioxane resins; lauryl methicone copolyol, perfluorononyl dimethicone, dimethicone/trisiloxane, methyl trimethicone, and combinations thereof. In one embodiment, the composition will comprise a shine-enhancing agent in an amount from about 0.1% to about 10% by weight, more preferably from about 1% to about 5% by weight, based on the total weight of the composition.

The cosmetic compositions of the invention may optionally include one or more waxes. The one or more waxes can be natural (e.g., vegetable, animal, or mineral) waxes or synthetic waxes (e.g., polyolefin, Fisher Tropsch, etc.). Suitable waxes that may be mentioned include, without glyceryl tribehenate, candelilla, carnauba, ozokerite, paraffin, polyethylene, microcrystalline wax, beeswax, ceresin, hydrogenated castor oil, japan wax, and mixtures thereof. In one embodiment, the amount of wax is from about 0.1 wt % to about 25 wt % of the total weight of the composition. In another embodiment, the amount of wax ranges from about 1% to about 20% by weight based on the total weight of the composition. In another embodiment the composition may comprise wax from about 5% to about 15% by weight based on the weight of the composition. In other embodiments the compositions may be wax free or substantially wax free (e.g., less than 1%, or less than 0.5%, or less than 0.25%, or less than 0.1% wax by weight of the composition).

The compositions of the invention may comprise one or more film formers, for example a hydrophobic film-former. The hydrophobic film former may be any hydrophobic material suitable for use in a cosmetic composition including, waxes, oils, and hydrophobic film-forming polymers. The term film-forming polymer may be understood to indicate a polymer which is capable, by itself or in the presence of at least one auxiliary film-forming agent, of forming a continuous film which adheres to a surface and functions as a binder for the particulate material. The term "hydrophobic" film-forming polymer will typically refer to a polymer with a solubility in water at 25° C. of less than about 1% by weight or one in which the monomeric units of the polymer individually have a solubility in water of less than about 1% by weight at 25° C. A "hydrophobic" film forming polymer will partition predominately into the octanol phase when shaken with a mixture of equal volumes of water and octanol. By predominately is meant more the 50% by weight, but preferably more than 75% by weight, more preferably more than 95% by weight will partition into the octanol phase.

Polymeric film formers include polyolefins, polyvinyls, acrylates, alkyl acrylates, polyurethanes, silicones, silicone acrylates, silicone polyurethanes, polyamides, polyimides, polyesters, fluoropolymers, polyethers, polyacetates, polycarbonates, rubbers, epoxys, formaldehyde resins, and homopolymers and copolymers of any of the foregoing.

Other polymeric film formers include silicon-containing polymers, including without limitation, dimethicone, dimethiconol, Amino Bispropyl Dimethicone, Aminopropyl Dimethicone, amodimethicone, Amodimethicone Hydroxystearate, Behenoxy Dimethicone, $C_{30-45}$ Alkyl Dimethicone, $C_{24-28}$ Alkyl Dimethicone, $C_{30-45}$ Alkyl Methicone, Cetearyl Methicone, Cetyl Dimethicone, Dimethoxysilyl Ethylenediaminopropyl Dimethicone, Hexyl Methicone, Hydroxypropyldimethicone, Stearamidopropyl Dimethicone, Stearoxy Dimethicone, Stearyl Methicone, Stearyl Dimethicone, Vinyl Dimethicone, Dimethicon/Polyalkylene Ether crosspolymers and copolymers, such as Dimethicone copolymers with PEG and/or PPG.

In some embodiments, it may be desirable to add some amount of a hydrophilic or water-soluble film former (e.g., cellulosics, polysaccharides, polyquaterniums, etc.) to the composition to improve spreading, emulsion stability, aesthetic look and feel, etc. In some embodiments, the collective weight percentage of hydrophilic or water-soluble film formers will be from about 0.001% by weight to less than about 20%, preferably less than about 15%, more preferably less than about 10%, and more preferably still, less than about 5% by weight based on the total weight of the composition.

Combinations of any of the foregoing film formers are also contemplated to be suitable, including combinations or polymeric and non-polymeric film formers and/or combinations of hydrophobic and hydrophilic film forming polymers. The film formers, when present, typically will comprise from about 0.01% to about 20% by weight of the composition, and more typically from about 0.5% to about 10% by weight of the composition.

The cosmetic compositions will typically comprise a physiologically acceptable vehicle. By "physiologically acceptable" is meant that the vehicle is safe for contact with human integuments. It is contemplated that any acceptable vehicle known in the art will be useful. The vehicle may comprise water, hydrophobic organic solvents and/or hydrophilic organic solvents. Suitable hydrophilic solvents include but are not limited to, lower alcohols (e.g., $C_2$-$C_6$ alcohols, such as ethanol); and glycols such as butylene glycol, propylene glycol, pentylene glycol, caprylyl glycol, and the like. The vehicle may comprise an oil, including for example, a hydrocarbon oil, ester oil, fatty alcohols and esters, and/or silicone oil. Suitable oils include ester oils, for example, vegetable oils; esters such as octyl palmitate, isopropyl myristate and isopropyl palmitate; ethers include dicapryl ether; fatty alcohols include cetyl alcohol, stearyl alcohol and behenyl alcohol; silicone oils include dimethicones, cyclic silicones, cyclomethicone pentamer, and polysiloxanes; hydrocarbon oils such as mineral oil, petrolatum, isoeicosane and polyisobutene; isoparaffins such as isooctane, isododecane, and isohexadecane, and squalane; additional natural or synthetic waxes; and the like. Suitable hydrophobic hydrocarbon oils may be saturated or unsaturated, have an aliphatic character and be straight or branched chained or contain alicyclic or aromatic rings. The oil-containing phase may be composed of a singular oil or mixtures of different oils. Special mention may be made of squalane and isododecane (IDD).

The compositions according to the invention may be formulated as water-in-oil (W/O) emulsions, oil-in-water (O/W) emulsions, water-in-silicone, silicone-in-water emulsions, and the like. These emulsions comprise a continuous phase and a discontinuous phase. The continuous phase may be aqueous, oil-based, or silicone-based and the discontinuous phase may likewise be aqueous, oil-based, or silicone-based, depending on the nature of the continuous phase. Combined oil and silicone phases are also possible.

The oil phase may comprise any of the hydrophobic oils discussed herein, including, without limitation, vegetable oils; fatty acid esters; fatty alcohols; isoparaffins such as isododecane; silicone oils such as dimethicones, cyclic silicones, and polysiloxanes; hydrocarbon oils such as mineral oil, petrolatum, isoeicosane and polyisobutene; natural or synthetic waxes; and the like.

Emulsions will typically comprise an amount of emulsifier sufficient to stabilize the emulsion. Suitable emulsifiers are listed in U.S. Pat. No. 8,168,640, the disclosure of which is hereby incorporated by reference. The amount of emulsifier will typically be from about 0.001 wt % to about 20 wt %, but preferably will range from about 0.01 to about 10 wt %, and most preferably about 0.1 wt % to about 5 wt %, based upon the total weight of the composition.

The carrier (vehicle) will typically comprise from about 1% to about 99% by weight of the composition, and more typically between about 30% and about 80% by weight. In some embodiments, the carrier comprises between about 50% and about 70% by weight of the composition. The vehicle may be aqueous or anhydrous. By "anhydrous" is meant that no water is intentionally added to the formulation but does not exclude minor amounts of water associated with the other components as impurities. Substantially anhydrous means less than 2.5% by weight water, typically less than 1% by weight water, and more typically, less than 0.5% by weight water, based on the entire weight of the composition.

A composition as described herein may also comprise other components that may be chosen depending on the vehicle and/or the intended use of the composition. Additional components include, but are not limited to, antioxidants (e.g., BHT); oil phase structurants, water phase structurants, gelants (e.g., ester terminated polyesteramides, polyamides, dibutyl ethyl hexamoyl glutamide and dibutyl lauroyl glutamide); chelating agents (e.g., disodium EDTA and citrate); emulsion stabilizers (e.g., carbomer); preservatives (e.g., methyl paraben or caprylyl glycol); fragrances (e.g., limonene, pinene, etc.); flavoring agents (e.g., sorbitol); humectants (e.g., glycerine); waterproofing agents (e.g., PVP/Eicosene copolymer); water soluble film-formers (e.g., hydroxypropyl methylcellulose); oil-soluble film formers; moisturizing agents, (e.g., cholesterol); cationic polymers (e.g., Polyquaterniums); anionic polymers (e.g., xanthan gum); pigment wetting agents, such as ARLACEL® P100, or EMEREST® 2452; vitamins (such as tocopherol and tocopherol acetate); and the like.

The compositions may comprise additional active ingredients having anti-aging benefits. Exemplary anti-aging components include, without limitation, botanicals; thiodipropionic acid (TDPA) and esters thereof; retinoids (e.g., all-trans retinoic acid, 9-cis retinoic acid, phytanic acid, retinol and others); hydroxy acids (including alpha-hydroxyacids and beta-hydroxyacids), salicylic acid and salicylates; exfoliating agents (e.g., glycolic acid, 3,6,9-trioxaundecanedioic acid, etc.), estrogen synthetase stimulating compounds (e.g., caffeine and derivatives); compounds capable of inhibiting 5 alpha-reductase activity (e.g., linolenic acid, linoleic acid, finasteride, and mixtures thereof); barrier function enhancing agents (e.g., ceramides, glycerides, cholesterol and its esters, alpha-hydroxy and omega-hydroxy fatty acids and esters thereof, etc.); collagenase inhibitors; and elastase inhibitors; to name a few.

Exemplary retinoids include, without limitation, retinoic acid (e.g., all-trans or 13-cis) and derivatives thereof, retinol (Vitamin A) and esters thereof, such as retinyl palmitate, retinyl acetate and retinyl propionate, and retinal.

In another embodiment, the topical compositions of the present invention may also include one or more of the following: a skin penetration enhancer, an emollient, a skin plumper, an exfoliating agent, or an antioxidant. In some embodiments, the compositions of the present invention may be utilized as UV protectants on any matter of surfaces, for example wood or leather surfaces, alone or in combination with other compositional components (paints, varnishes, etc.) typically utilized in such materials.

An emollient provides the functional benefits of enhancing skin smoothness and reducing the appearance of fine lines and coarse wrinkles Examples include isopropyl myristate, petrolatum, isopropyl lanolate, silicones (e.g., methicone, dimethicone), oils, petrolatum, mineral oils, fatty acid esters, cetyl ethylhexanoate, $C_{12-15}$ alkyl benzoate, isopropyl isostearate, diisopropyl dimer dillinoeate, or any mixtures thereof. Other emollients include jojoba oil, lanolin oil, coconut oil, palm kernel glycerides, grape seed oil, evening primrose oil, sesame oil, castor oil, meadowfoam seed oil, emu oil, dimethicone copolyol meadowfoamate, wheat germ oil, macadamia nut oil, avocado oil, and mixtures thereof. The emollient may be present from about 0.1 wt % to about 50 wt % of the total weight of the composition. More typically, emollients will be present in an amount from about 2 wt % to about 15 wt %, preferably, about 5 wt %.

A skin plumper may also be included. An example of a suitable skin plumper is palmitoyl oligopeptide. Other skin plumpers are collagen and/or other glycosaminoglycan (GAG) enhancing agents. When present, the skin plumper will typically comprise from about 0.1 wt % to about 20 wt % of the total weight of the composition.

Suitable exfoliating agents include, for example, alpha-hydroxyacids, beta-hydroxyacids, oxaacids, oxadiacids, and their derivatives such as esters, anhydrides and salts thereof. Suitable hydroxy acids include, for example, glycolic acid, lactic acid, malic acid, tartaric acid, citric acid, 2-hydroxyalkanoic acid, mandelic acid, salicylic acid and derivatives thereof. In one embodiment an exfoliating agent is glycolic acid. When present, the exfoliating agent may comprise from about 0.1 wt % to about 20 wt % of the composition.

Antioxidants scavenge free radicals from skin, protecting the skin from environmental aggressors. Examples of antioxidants that may be used in the present compositions include compounds having phenolic hydroxy functions, such as ascorbic acid and its derivatives/esters; alpha-hydroxyacids; beta-carotene; catechins; curcumin; ferulic acid derivatives (e.g. ethyl ferulate, sodium ferulate); gallic acid derivatives (e.g., propyl gallate); lycopene; reductic acid; rosmarinic acid; tannic acid; tetrahydrocurcumin; tocopherol and its derivatives (e.g., tocopheryl acetate); uric acid; or any mixtures thereof. Other suitable antioxidants are those that have one or more thiol functions (—SH), in either reduced or non-reduced form, such as glutathione, lipoic acid, thioglycolic acid, and other sulfhydryl compounds. The antioxidant may be inorganic, such as bisulfites, metabisulfites, sulfites, or other inorganic salts and acids containing sulfur. A preferred antioxidant is thiodipropionic acid or fatty esters (e.g., dilaurate) thereof. Compositions of the present invention may comprise an antioxidant in one embodiment from about 0.001 wt % to about 10 wt %, and in one embodiment from about 0.01 wt % to about 5 wt %, of the total weight of the composition.

Other conventional additives include: vitamins, such as tocopherol and ascorbic acid and esters thereof; vitamin derivatives such as tocopherol acetate and ascorbyl palmitate; thickeners such as hydroxyalkyl cellulose; gelling agents; structuring agents such as bentonite, smectite, magnesium aluminum silicate and lithium magnesium silicate; metal chelating agents such as EDTA; pH adjusters (including NaOH, KOH, trialkyl amines, citric acid, phosphoric acid, hydrochloric acid, ammonium chloride, etc.)

A composition comprising organic sunscreen, nylon, silica, and barium sulfate may be used in any type of hair treatment, lip product, skin treatment or makeup product. Such makeup products may include, but are not limited to, foundations, blushes, pressed or loose powders, concealers, bronzers, eyeshadows, and eyeliners. Lip products include without limitation lipsticks, lip colors, lip balms, and lip glosses. A composition as described herein may take any form which is typical of cosmetic products, for example, anhydrous compositions, aqueous systems, hot pour systems, emulsions, gels, sticks, sprays, and pressed or loose powders. There is essentially no limitation on the type of vehicle that may be employed although it should be physiologically acceptable for contact with a human integument.

Methods for protecting a human integument against UV damage comprising applying to the integument a composition of the present invention are also encompassed by the invention. In some embodiments, the compositions are applied to a human integument, such as the skin of the face, hands, body, or lips.

EXAMPLES

Example 1

Compositions 1-22 were prepared according to base formula of Table 1. The nylon, silica, and barium sulfate were either absent or present in the indicated amount depending on the sample, as shown in Tables 2-4. The Nylon particles were porous nylon-6 particles treated with hydrogen dimethicone (POMP 605-S101 from UBE Industries). The silica particles were spherical silica available from Kobo Products as MSS-500W. Barium sulfate particles were either "USP Barium Sulfate for Formulation" from Mallinckrodt Inc or "Blanc Fixe XR-HN" from Sachtleben Chemie GmbH.

Tables 2-4 indicate the presence (+) or absence (−) of an organic sunscreen, barium sulfate, nylon, silica, or iron oxide in each composition. When present, the amount of barium sulfate was 5 wt %, the amount of nylon was 5 wt %, the amount of silica was 2.5 wt %, and the amount of OMC was 7.5 wt %, and the amounts of homosalate and octyl salicylate were each 5 wt %. For compositions where a component was omitted, castor oil was used to replace the omitted component and q.s. to a total of 100%.

TABLE 1

| Phase | Ingredient | Percent |
|---|---|---|
| A | Castor Oil | q.s. |
|   | Diglyceryl Diisostearate | 10.5 |
|   | Squalane | 10 |
|   | Glyceryl Triacetyl Hydroxystearate | 7.9 |
|   | Myristyl Lactate | 7.5 |
|   | C10-30 Cholesterol/Lanosterol Esters | 4.5 |
|   | Polybutene | 3.2 |
|   | Polyglycerol Diisostearate | 3 |
|   | PPG-51/SMDI Copolymer | 2.5 |
|   | Stearyl Dimethicone | 2.5 |
|   | Ozokerite | 5.45 |
| B | Micro Wax | 5 |
|   | Polyethylene | 3 |
|   | Caprylyl Glycol | 0.5 |
| C | Red iron oxide | 0 or 0.50 |
|   | Titanium Dioxide | 0.33 |
|   | Barium Sulfate | 0 or 5.0 |
| D | Nylon-6 | 0 or 5.0 |
|   | Silica Particles | 0 or 2.5 |
| E | OMC | 0 or 7.5 |
|   | Homosalate | 0 or 5.0 |
|   | Octyl Salicylate | 0 or 5.0 |

The samples were prepared as follows. Phase A, Phase C and Phase D ingredients were combined and mixed until uniform, then added to pre-melted waxes of Phase B. Phase E was then added, mixed until uniform, and cooled.

An in vitro SPF spectrometer was used to measure in vitro SPF of the formulas. A 0.5 ml thick draw down was made on 3M Transpore™ Tape (2 in×2 in of tape), which was placed onto 2 mm thick Quartz plates. The SPF was measured on a Labsphere UV Transmittance Analyzer by taking the average of 5 measurements on 3 plates per sample.

Diffuse transmittance was measured on the X-rite Color i7 Spectrophotometer. Samples were prepared by making drawdowns of 3 mL film thickness of each composition on glass plates. The samples were allowed to sit for 4 hours before measurements were taken. Total transmittance was measured along with direct transmittance. Diffuse transmittance is calculated by taking the difference between the two measurements.

The results of the SPF and diffuse transmittance measurements on several different samples are shown below in Table 2.

TABLE 2

|   | 1 | 2 | 3 | 4 | 5 | 6 | 7 | 8 | 9 | 10 |
|---|---|---|---|---|---|---|---|---|---|---|
| OMC | + | + | − | − | − | − | + | + | + | + |
| Nylon | − | + | − | − | + | + | − | − | + | + |
| Silica | − | + | − | − | + | + | − | − | + | + |
| Barium Sulfate | − | + | − | − | + | + | − | − | + | + |
| Iron Oxide, uncoated | − | − | − | + | − | + | − | + | − | + |
| Iron Oxide, silica-coated | − | − | + | − | + | − | + | − | + | − |
| SPF | 15.04 | 20.21 | 1.79 | 1.71 | 1.39 | 1.53 | 18.94 | 16.43 | 35.69 | 30.05 |
| Diffuse Transmittance | 27.01 | 56.18 | 40.13 | 39.1 | 50.85 | 49.63 | 38.69 | 35.02 | 50.55 | 42.38 |

It can be seen from Table 2 that the presence of barium sulfate, silica and nylon in the presence of an organic sunscreen boosts SPF by at least 5 units (sample #1 versus sample #2). The SPF enhancing effect is more pronounced in the presence of iron oxide (sample #8 versus sample #10) providing an SPF boost of 13.5 units, while the most pronounced increase of 16.75 SPF units is observed in the presence of silica-coated iron oxide (sample #7 vs. sample #9). The SPF increases from 30.05 to 35.69 for sample #9 versus sample #10 with the addition of silica-coated red iron oxide in place of uncoated red iron oxide. Additionally, diffuse transmittance is enhanced when nylon, silica, and barium sulfate are present, yielding values greater than 40 units and ideally about 50 units or greater.

Example 2

Samples #11-14 were prepared to assess the role of each of the three components (barium sulfate, nylon, and silica) in enhancing SPF of an organic sunscreen. Sample #11 contained 7.5% OMC, 0.50% silica-coated iron oxide, 5% nylon and 2.5% silica, without barium sulfate. Sample #12 contained 7.5% OMC, 0.50% silica-coated iron oxide, and 5% nylon, without silica and barium sulfate. Sample #13 contained 7.5% OMC, 0.50% silica-coated iron oxide, and 2.5% silica, without nylon and barium sulfate. Sample #14 contained 7.5% OMC, 0.50% silica-coated iron oxide, and 5% barium sulfate, without nylon and silica. Samples #11-14 were evaluated for SPF and diffuse transmittance according to the procedure above. The data is summarized below, along with sample #9 (containing all three components) for comparison.

TABLE 3

|   | 7 | 9 | 11 | 12 | 13 | 14 |
|---|---|---|---|---|---|---|
| OMC | + | + | + | + | + | + |
| Nylon | − | + | + | + | − | − |
| Silica | − | + | + | − | + | − |
| Barium Sulfate | − | + | − | − | − | + |
| Iron Oxide, silica-coated | + | + | + | + | + | + |
| SPF | 18.94 | 35.69 | 23.02 | 22.26 | 22.30 | 24.25 |
| Diffuse Transmittance | 38.69 | 50.55 | 49.27 | 46.71 | 35.75 | 47.93 |

Sample #9, (containing nylon, silica, and barium sulfate), gave an SPF of 35.69. Samples #11-14, which lack one or more of the three components, gave SPF values ranging from 22-24. The striking increase of SPF by more than 10 SPF units for sample #9 is greater than an additive effect of each of the three components, demonstrating a synergy of nylon, silica, and barium sulfate when used together to boost SPF of an organic sunscreen.

Example 3

Samples #15-22 were prepared to study the effect of the three-component system with other organic sunscreens, namely, homosalate and octyl salicylate.

TABLE 4

|  | 15 | 16 | 17 | 18 | 19 | 20 | 21 | 22 |
|---|---|---|---|---|---|---|---|---|
| OMC | + | + | − | − | + | + | − | − |
| Homosalate | + | + | + | + | − | − | − | − |
| Octyl salicylate | − | − | − | − | + | + | + | + |
| Nylon | + | − | + | − | + | − | + | − |
| Silica | + | − | + | − | + | − | + | − |
| Barium Sulfate | + | − | + | − | + | − | + | − |
| Iron Oxide, silica-coated | + | + | + | + | + | + | + | + |
| SPF | 28.33 | 22.63 | 12.21 | 7.72 | 24.63 | 21.40 | 12.65 | 9.44 |
| Transmittance Diffuse | 52.93 | 40.03 | 54.83 | 38.23 | 54.13 | 40.07 | 55.26 | 39.16 |

Octyl salicylate (5%) or homosalate (5%), were added with or without OMC to the samples with or without nylon, silica, and barium sulfate. Comparing sample #15 to #16, #17 to #18, #19 to #20, and #21 to #22, the in vitro SPF is higher in all samples containing nylon, silica, and barium sulfate vs. their respective controls without the three components, indicating that the combination boosts SPF of other organic sunscreens.

Example 4

Samples #23 and #24 were prepared to study the effect of the three-component system in an oil-in-water emulsion formulation. The samples were prepared according to the formula of Table 5. The nylon, silica, and barium sulfate were either absent or present in the indicated amount, as shown in Table 6. The Nylon particles were porous nylon-6 particles treated with hydrogen dimethicone (POMP 605-S101 from UBE Industries). The silica particles were spherical silica available from Kobo Products as MSS-500W. Barium sulfate particles were either "USP Barium Sulfate for Formulation" from Mallinckrodt Inc or "Blanc Fixe XR-HN" from Sachtleben Chemie GmbH. Samples #23 and #24 contained the following organic sunscreens: Octyl Salicylate, Homomenthyl Salicylate, Benzophenone-3 (Oxybenzone), Butyl Methoxydibenzoylmethane, and Octocrylene. The preparation and testing procedures were identical to those of Example 1.

TABLE 5

| Ingredient | Percent |
|---|---|
| Demineralized Water | q.s. |
| Disodium Edta | 0.2 |
| Acrylates/C10-30 Alkyl Acrylate Crosspolymer Carbopol 940 | 0.2 0.25 |
| Butylene Glycol | 1.5 |
| Glycerin | 3.0 |
| Methylparaben | 0.4 |
| Sodium Dehydroacetate | 0.1 |
| Lecithin | 0.3 |
| Polyethylene Glycol | 3.0 |
| Octyl Salicylate | 4.75 |
| Octyl Isononanoate | 1.0 |
| Homomenthyl Salicylate | 8.0 |

TABLE 5-continued

| Ingredient | Percent |
|---|---|
| Benzophenone-3 (Oxybenzone) | 5.5 |
| Butyl Methoxydibenzoylmethane | 2.8 |
| Octocrylene | 2.5 |
| Polyglyceryl-3 Diisostearate | 0.2 |
| Cetyl Alcohol | 0.6 |
| Poe (24) Cholesterol Ether | 0.125 |
| Glyceryl Stearate Monoester | 0.4 |
| Fumed Silica | 0.1 |
| Dimethyl/Trimethyl Polysiloxane | 1.0 |
| Barium Sulfate | 0 or 1.25 |
| Nylon 6 | 0 or 1.25 |
| Silica | 0 or 0.625 |
| Isododecane | 1.5 |
| Silicone Resin | 0.12 |
| Triethanolamine 99% | 0.6 |
| Phenoxyethanol | 0.5 |

TABLE 6

|  | 23 | 24 |
|---|---|---|
| Sunscreen | + | + |
| Nylon | + | − |
| Silica | + | − |
| Barium Sulfate | + | − |
| Iron Oxide, silica-coated | − | − |
| SPF | 37.0 | 31.2 |

As shown in Table 6, the in vitro SPF was about 20% higher in sample #23 (SPF of 37.0), which contained nylon, silica, and barium sulfate, as compared to the control sample #24 without the three components (SPF of 31.2), indicating that the SPF-boosting combination is effective in oil-in-water emulsion formulations.

Example 5

Samples #25, #26 and #27 were prepared to study the effect of using different nylon particles. The samples were prepared according to the formula of Table 7. The nylon, silica, and barium sulfate were either absent or present in the indicated amount, as shown in Table 6. The Nylon particles were either porous nylon-6 particles treated with hydrogen dimethicone (POMP 605-S101 from UBE Industries) or non-porous nylon-12 particles (Nylon SP-500 distributed by Kobo Products, Inc.) lacking a surface treatment. The silica particles were spherical silica available from Kobo Products, Inc. as MSS-500W. Barium sulfate particles were either "USP Barium Sulfate for Formulation" from Mallinckrodt Inc or "Blanc Fixe XR-HN" from Sachtleben Chemie GmbH. Samples #25-27 contained 7.5% ethylhexyl-methoxycinnamate (OMC) and 0.5% silica-coated red iron oxide. The preparation and testing procedures were identical to those of Example 1.

TABLE 7

| Ingredient | Percent |
| --- | --- |
| Castor Oil | q.s. |
| Diglyceryl Diisostearate | 10.5 |
| Squalane | 10 |
| Glyceryl Triacetyl Hydroxystearate | 7.9 |
| Myristyl Lactate | 7.5 |
| C10-30 Cholesterol/Lanosterol Esters | 4.5 |
| Polybutene | 3.2 |
| Polyglycerol Diisostearate | 3 |
| PPG-51/SMDI Copolymer | 2.5 |
| Stearyl Dimethicone | 2.5 |
| Ozokerite | 5.45 |
| Micro Wax | 5 |
| Polyethylene | 3 |
| Caprylyl Glycol | 0.5 |
| Titanium dioxide | 0.33 |
| OMC | 7.5 |
| Silica-coated red iron oxide | 0.5 |
| Porous Nylon 6 | 0 or 5.0 |
| Non-porous Nylon 12 | 0 or 5.0 |
| Silica | 0 or 2.5 |
| Barium Sulfate | 0 or 5.0 |

TABLE 8

|  | 25 | 26 | 27 |
| --- | --- | --- | --- |
| Sunscreen | + | + | + |
| Iron Oxide, silica-coated | + | + | + |
| Porous Nylon-6 | − | + | − |
| Non-Porous Nylon 12 | − | − | + |
| Silica | − | + | + |
| Barium Sulfate | − | + | + |
| SPF | 20.2 | 30.5 | 29.4 |
| Diffuse Transmittance | 40.28 | 44.99 | 46.39 |

As shown in Table 8, the in vitro SPF of samples #26 and #27 which contained nylon, silica, and barium sulfate, was about 50% higher than that of sample #25 without the three components. The SPF observed for sample #26 prepared with porous nylon particles was not significantly different than that observed for sample #27 prepared with non-porous nylon particles.

The invention claimed is:

1. A composition comprising an organic sunscreen and an SPF-boosting composition comprising:
   (i) nylon particles;
   (ii) silica particles; and
   (iii) barium sulfate particles,
   wherein the SPF-boosting composition provides an increase in SPF as compared to an otherwise identical combination lacking any one of the three components, (i)-(iii), wherein said nylon particles comprise from about 1% to about 10% by weight of the composition; said silica particles comprise from about 0.5% to about 5% by weight of the composition; and said barium sulfate particles comprise from about 1% to about 10% by weight of the composition, and wherein the weight ratio of components (i) to (ii) to (iii) is about 5-15:1-10:5-15.

2. A composition according to claim 1, wherein the weight ratio of components (i) to (ii) to (iii) is about 2:1:2.

3. A composition according to claim 1, wherein said nylon particles are surface treated with hydrogen dimethicone.

4. A composition according to claim 1, wherein said nylon particles comprise porous nylon-6 particles.

5. A composition according to claim 1, wherein said nylon particles comprise porous nylon-6 particles surface treated with hydrogen dimethicone.

6. A composition according to claim 1, wherein said silica particles are spherical.

7. A composition according to claim 1, further comprising a pigment.

8. A composition according to claim 5, wherein said pigment is iron oxide.

9. A composition according to claim 6, wherein said iron oxide is coated with silica.

10. A composition according to claim 1, wherein the boost in SPF is at least about 10%.

11. A composition according to claim 1, wherein the organic sunscreen is selected from ethylhexyl-methoxycinnamate, homosalate, octyl salicylate, oxybenzone, octocrylene and Avobenzone.

12. A composition according to claim 1, wherein said composition achieves diffuse transmittance of at least 40.

13. A composition according to claim 1, wherein said composition is anhydrous.

14. A composition according to claim 1, wherein said composition comprises an oil-in-water emulsion.

15. A method for protecting a human integument against UV damage comprising applying to said integument a composition comprising an organic sunscreen and an SPF-boosting composition comprising:
   (i) nylon particles;
   (ii) silica particles; and
   (iii) barium sulfate particles,
   wherein the SPF-boosting composition provides an increase in SPF as compared to an otherwise identical combination lacking any one of the three components, (i)-(iii), wherein said nylon particles comprise from about 1% to about 10% by weight of the composition; said silica particles comprise from about 0.5% to about 5% by weight of the composition; and said barium sulfate particles comprise from about 1% to about 10% by weight of the composition, and wherein the weight ratio of components (i) to (ii) to (iii) is about 5-15:1-10:5-15.

* * * * *